United States Patent [19]

Honma et al.

[11] Patent Number: 4,966,158

[45] Date of Patent: Oct. 30, 1990

[54] MEASUREMENT METHOD FOR MOISTURE CONTENT IN THE SKIN AND SYSTEM THEREFOR

[75] Inventors: Yasuhiro Honma, Ichikawa; Nobuo Miyazaki, Yokohama; Hisashi Misumi, Utsunomiya; Toshiyasu Suda, Chiba; Shuichi Akazaki, Funabashi; Yoshihiro Minematsu, Funabashi; Michio Kawai, Funabashi, all of Japan

[73] Assignee: Kao Corporation, Tokyo, Japan

[21] Appl. No.: 271,015

[22] Filed: Nov. 14, 1988

[30] Foreign Application Priority Data

Nov. 12, 1987 [JP] Japan .................. 62-285780

[51] Int. Cl.⁵ ............................................ A61B 5/05
[52] U.S. Cl. .................... 128/734; 324/664; 324/688; 324/689; 324/692; 324/696
[58] Field of Search ................ 128/639–640, 128/734, 741, 419 R, 421, 422, 783, 802, 798; 324/65 R, 664, 688, 689, 692, 694, 696, 715

[56] References Cited

U.S. PATENT DOCUMENTS

| 4,252,130 | 2/1981 | Le Pivert | 128/734 |
| 4,494,554 | 1/1985 | Van Dyke et al. | 128/734 |
| 4,540,002 | 9/1985 | Atlas | 128/734 |

FOREIGN PATENT DOCUMENTS 59-28646  2/1984  Japan .

OTHER PUBLICATIONS

Dahmen, "Measuring the Contact Resistance of Metallization on Silicon", IBM Technical Disclosure Bulletin, vol. 15, No. 5, Oct., 1972, p. 1492.

Primary Examiner—Ruth S. Smith
Attorney, Agent, or Firm—Cushman, Darby & Cushman

[57] ABSTRACT

This invention relates to the measurement of the moisture content retained in the skin, and enables accurate diagnosis of the skin conditions by a device which can be switched in the connection of measurement electrodes to measure the moisture content either in the surface or in the depth of the keratinous layer of the skin.

6 Claims, 7 Drawing Sheets

PRIOR ART

PRIOR ART

MEASUREMENT METHOD FOR MOISTURE CONTENT IN THE SKIN AND SYSTEM THEREFOR

TECHNICAL FIELD OF THE INVENTION

This invention is applicable to the measurement of moisture content in the skin.

This invention relates to a method and a device for measuring the moisture content in the human skin or the keratinous layer. More particularly, this invention relates to a method of not only measuring moisture content in the surface of the keratinous layer but also detecting the moisture retained in the deeper layer so as to more accurately learn the conditions of the skin.

PRIOR ART

Figures 6, 7:
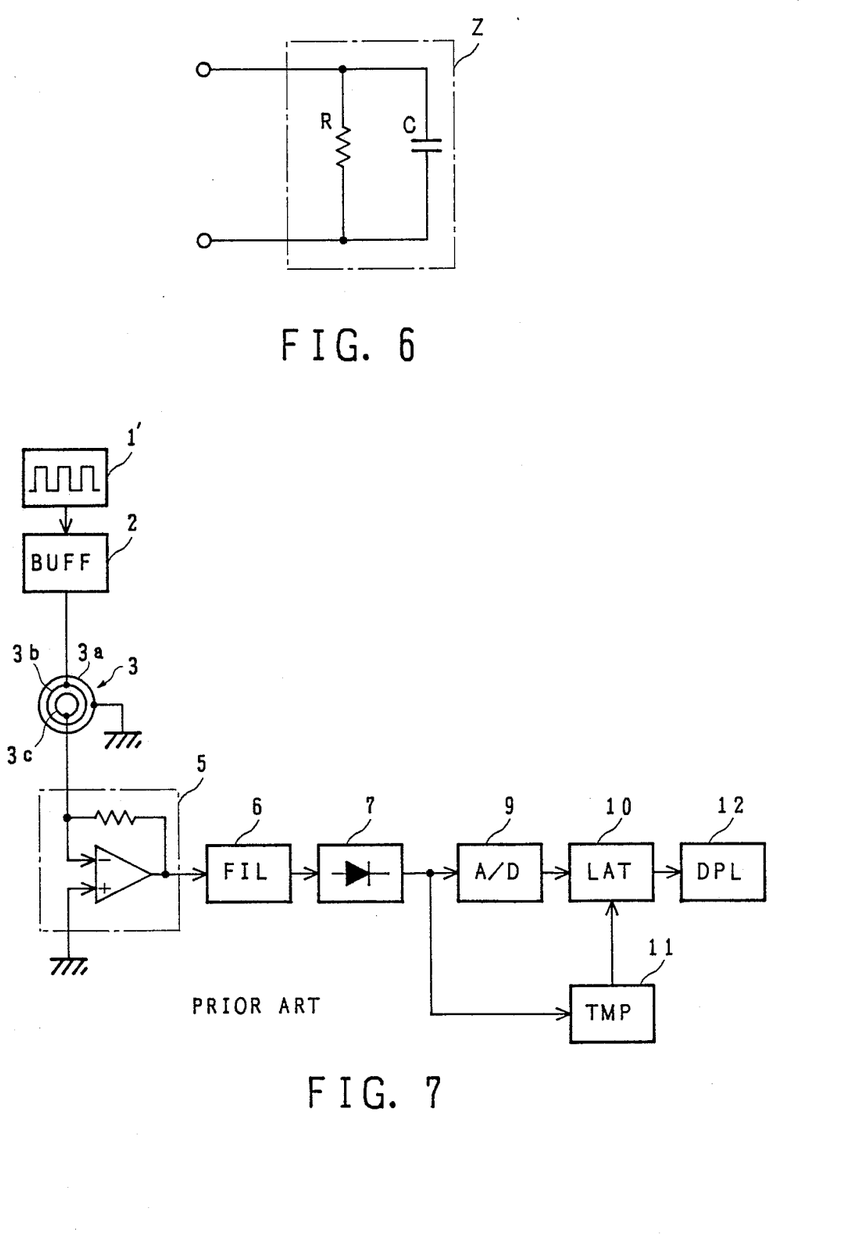

There has been known a technology to measure the moisture content in the keratinous layer by sending weak high-frequency current through the human skin and measuring the impedance generated on the skin surface. An equivalent circuit responsive to the high frequency current through the keratinous layer generally comprises parallel circuits of a resistor R and a capacitor C as shown in FIG. 6. When the moisture content in the layer changes, the resistance R and capacity C will change. Detailed description on the above phenomenon is found in, for instance, Y. Masuda, M. Nishikawa, B. Ichijo, I.E.E.E. Trans. Instrum. Meas. IM 29, No. 1, 28, 1980 and H. Tanoue, M. Ohi, M. Yamada, The Nishinihon Journal of Dermatology, Vol. 42, No. 4, P. 647, 1980.

The system for measuring these characteristics is a so-called impedance meter which measures the impedance of the equivalent circuit shown in FIG. 6 both in real component and in imaginary component separately.

$$Z = \frac{1}{\frac{1}{R} + jlC} \quad (1)$$

As the electrode used in the aforementioned prior art system is a single electrode, operation in measurement is inconveniently cumbersome, and when used to measure the human skin, the measured values fluctuate widely and unstably. As the size of the electrode is small, the scope of measurement is limited to the keratinous layer. In order to obviate such problems, the present inventors previously proposed a device which has a triple electrode structure, uses low frequency electric current of 3 KHz -100 KHz, is simple in structure and inexpensive (refer to Japanese Patent Application Laid-Open on Feb. 15, 1984 under No. Sho 59-28646 the content of which is incorporated hereinto by reference), and put it into practice.

FIG. 7 is a block diagram to show the circuit structure of the previously proposed device wherein rectangular-wave generator 1' has an output connected via a buffer circuit 2 to a measuring electrode structure 3 which is to be abutted onto the skin for detecting the moisture content. The measuring electrode structure 3 is constructed in the form of triple concentric circles. An electrode 3a on the outermost circle is grounded as a guard electrode so as to prevent noises induced on the human body. An intermediate electrode 3b is connected to said buffer circuit 2 while a central electrode 3c is connected to an amplifier 5. The output from the amplifier 5 is connected to a rectifier 7 via a filter circuit 6. The output from the rectifier 7 is connected to the input of a latch circuit 10 via an AD converter 9. The clock pulse of the latch circuit 10 is given from a timer 11 which is actuated by the output from said rectifier 7 and outputs the clock pulses after a predetermined time. The output from said latch circuit 10 is connected to a digital display circuit 12.

The above described device is operated as follows. The rectangular-wave signals generated by the generator 1' is shaped in waveform by the buffer 2 to stabilize its amplitude before it is given to the measuring electrode 3. The output of the buffer 2 is applied between the electrode 3b and ground.

Figure 8:
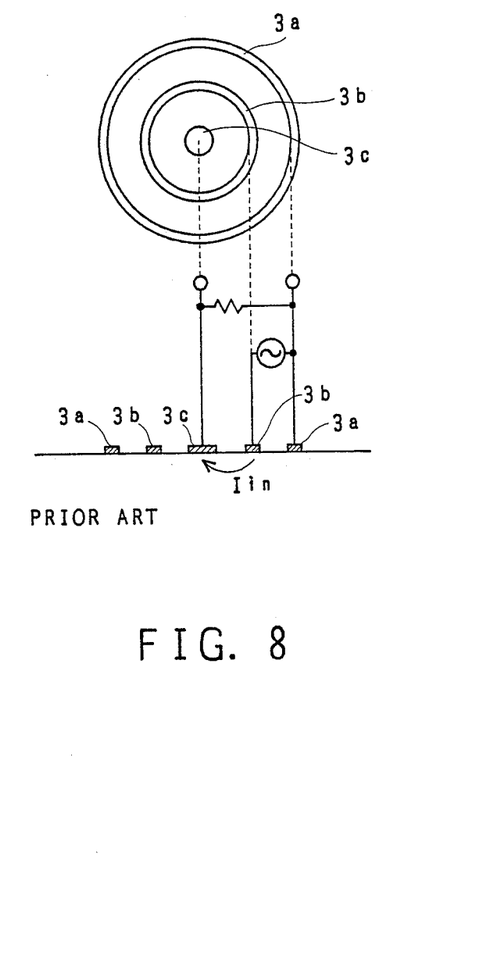

When the measuring electrode 3 is pressed onto the skin at a subject location, the potential difference between electrode 3a on the outermost circle and central electrode 3c changes due to the moisture content on the keratinous layer, which is detected in terms of voltage and amplified by the amplifier 5. Therefore, the output current from the buffer 2 passes between the electrode 3b and the electrode 3c as shown in FIG. 8, and the potential difference therebetween appears in the output from amplifier 5. Noise of short period are removed by filter 6.

The AC voltage filtered by filter 6 is transformed into DC current by rectifier 7. The DC current is digitized by an AD converter 9. The digitized signals are temporarily stored sequentially in latch circuit 10, and its digital output is displayed at a digital display circuit 12 at a predetermined timing clocked by the timer 11.

The above mentioned device can measure the moisture content in the keratinous layer with considerably high precision, but the device is still not fully free of the influence from the conditions on the skin surface. This is because the device is adapted to feed low frequency electric current between either the central electrode 3c or the intermediate electrode 3b, and the outer electrode 3a; and to measure the electric voltage produced between the other of said central electrode 3c and the intermediate electrode 3b, and the outer electrode 3a. Therefore, the produced voltage is greatly influenced by the current passing through the skin surface between the central electrode 3c and the intermediate electrode 3b as shown in FIG. 8. The same problem occurs if the central electrode 3c is grounded and the ungrounded input/output lines are respectively connected to electrodes 3b/3a or vice versa.

PURPOSE OF THE INVENTION

This invention is directed towards solving the problems encountered in the prior art and aims at providing a method and device which can measure the moisture content not only on the keratinous layer but also in the deeper part of the skin for more precise diagnosis of skin conditions.

DISCLOSURE OF THE INVENTION

The first aspect of this invention relates to a method and device which passes slight low-frequency current from two electrodes abutted onto the skin through the keratinous layer, amplifies the voltage appearing in the layer, and measures the rectified amplitude of that voltage to learn the moisture content in the keratinous layer, which is characterized in that the voltage appearing in said keratinous layer is the voltage appearing between one of said two electrodes and another electrode which is abutted onto the skin at a location between the two electrodes.

The second aspect of this invention relates to a measurement device for moisture content in the skin which device in detail comprises a triple concentric circular electrode structure including a central electrode, a common intermediate electrode and an outer electrode which can be abutted onto the skin surface, a generator which supplies low-frequency current between the common electrode and another one of the electrodes, an amplifier which amplifies the voltage appearing between said common electrode and still another electrode, and a means which displays the output voltage from the amplifier.

The third aspect of this invention relates in detail to a measurement device for moisture content in the skin comprising a triple concentric circular electrode structure including a central electrode, an intermediate electrode and an outer electrode which can be abutted onto the skin surface, a generator which supplies low-frequency current between one of said electrodes as a common electrodes and another one of said electrodes, an amplifier which amplifies the voltage appearing between said common electrode and still another one of said three electrodes, and a means which displays the output voltage from the amplifier, which is characterized in that a circuit means is provided for switching between a first circuit using said intermediate electrode as said common electrode and a second circuit which uses either one of said central electrode and said outer electrode as the common electrode.

It is preferable to provide two measurement electrodes one of which is connected to the first circuit and the other of which is connected to the second circuit.

Experiments disclosed that when the resistance and capacity which are supposed to change by the moisture content in the keratinous layer are compared to each other, if the low frequency current is selected in the range of 3 KHz to 100 KHz, the resistance is much more influenced than capacity by the changes of moisture content in the range which is assumed to be retained in the human skin. The moisture content in the keratinous layer can be measured to a considerable extent by measuring the absolute value $|Z|$ of impedance obtained from the equation below without the necessity to separate resistance from the capacity.

$$|Z| = \frac{R}{\sqrt{1 + (WCR)^2}} \quad (2)$$

The voltage which satisfies the equation (2) can be obtained by amplifying the primary voltage and rectifying it.

More specifically, when low-frequency current is supplied between either one of the central electrode and the outer electrode, and the intermediate electrode of the measurement electrode the structure of which forms substantially concentric triple circular electrodes and which can be abutted onto the skin, a voltage is generated between the other one (or the one not selected above) of the central electrode and outer electrode, and the intermediate electrode. Almost all the current flowing on the skin surface runs to the intermediate electrode without influencing the voltage generated between the intermediate electrode and the above mentioned other electrode. The current flowing in the depth of the keratinous layer runs toward said other electrode to greatly influence the voltage generated between the intermediate electrode and said other electrode of the central and outer electrodes. The moisture content in the depth of the layer can therefore be measured from the voltage.

The device may be equipped with measurement electrodes of different circuits which can be switched by a switch so that the moisture content in both the surface and the depth of the keratinous layer can be detected.

As described in the foregoing statement, this invention enables measurement of moisture content in the depth of the keratinous layer so as to learn the general moisture retention and retaining function of the keratinous layer as a whole.

If the whole measurement device according to this invention is made portable, it can be easily used without much trouble even by laymen without knowledge or expertise on the device.

The device is further advantageous if equipped with two types of electrodes of different circuits which are shifted with a switch, as it can be used to measure the moisture content in the layers both relatively close to the surface and relatively deep.

BRIEF DESCRIPTION OF DRAWINGS

FIG. 5 is a graph to show the characteristics of moisture detected on the human skin, FIG. 6 an equivalent circuit diagram on the keratinous layer, FIG. 7 a circuit diagram of a prior art device and FIG. 8 a diagram to show the structure and connection of the prior art measurement electrodes.

PREFERRED EMBODIMENTS

Figure 1:
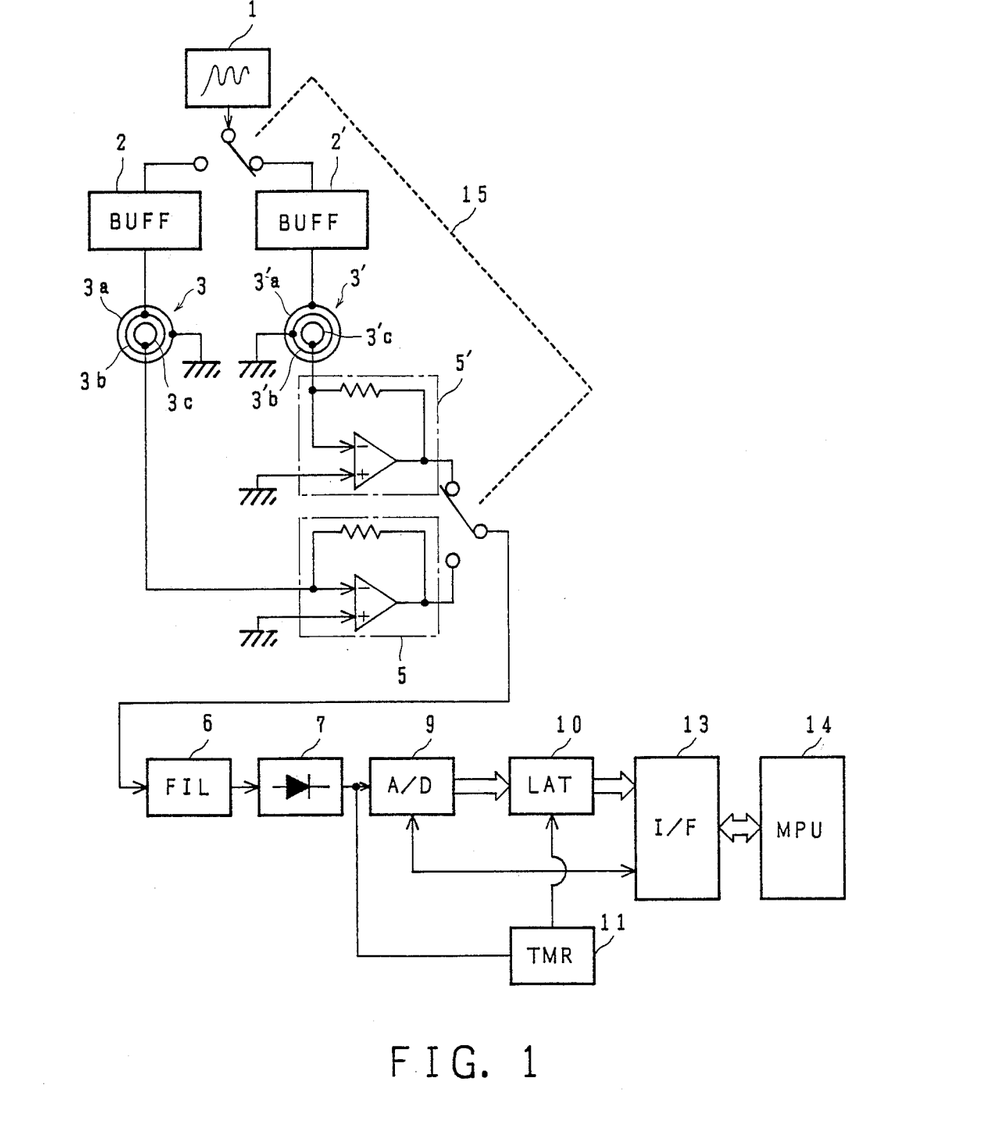
FIG. 1 is an electric circuit diagram to show an embodiment of this invention.

FIG. 1 is a circuit diagram of an embodiment of this invention wherein the output sine wave generator 1 is connected to a measurement electrode structure 3 or 3' via a switch 15 and a buffer 2 or 2'. Electrode structure 3 is used for measurement of the moisture content on the surface of keratinous layer, while electrode structure 3' is used for measurement of the moisture content in the depth of the keratinous layer by abutting the electrode structures onto the skin. The measurement electrode structures 3,3' are respectively connected to amplifiers 5,5'.

Description is now given to the case where the moisture contained in the depth of the keratinous layer is detected. The electrode structure 3' is structured to define triple concentric circles having a central electrode 3b' which is earthed as a guard electrode in order to eliminate the effect of the electric current flowing through the keratinous layer. To an outer electrode 3a' of the electrode structure 3' is connected a buffer 2' while an amplifier 5' is connected to a central electrode 3c'. The output from a rectifier 7 is connected to the input of a latch circuit 10 via an AD converter 9. A clock pulse is fed to latch circuit 10 from a timer 11 which is actuated with the output from said rectifier 7 to start the latch output after a predetermined time. The output from the latch circuit 10 is connected to a computer 14 via an interface 13.

In operation, sine wave signals generated at the sine wave generator 1 are shaped in the waveforms thereof and stabilized in amplitude by buffer 2' and are fed to the measurement electrode 3'. The output from the buffer 2' is applied between the electrode 3a' and ground. The voltage to be applied in the measurement electrode 3' is set at a level less than 3 V or any other level low enough not to be sensed by man. The frequency of the electric current generated by the generator 1 is selected from the range of 1–50 KHz or preferably from the range of 10–30 KHz so as to avoid polarization due to the moisture in the skin.

Figure 2:
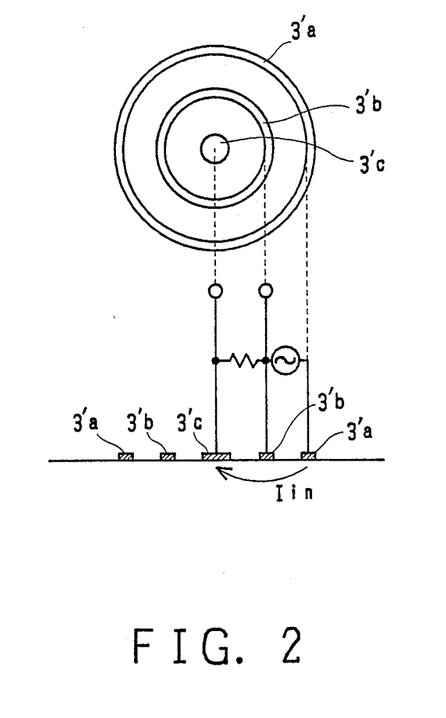
FIG. 2 a diagram to show the structure and connection of measurement electrode structure used for the embodiment of this invention, FIG. 3 a perspective view to show the embodiment of this invention, FIG. 4 a graph to show characteristics in moisture detection in a test using water permeable membrane.

When the measurement electrode 3' is abutted on the skin being tested, the potential difference between the intermediate electrode 3'b and the central electrode 3'c changes due to the moisture content in the deeper keratinous layer, and the voltage detected is amplified at the amplifier 5'. Therefore, the output current of the buffer 2' flows between the electrode 3'a and the electrode 3'c as shown in FIG. 2, and this potential difference appears at the output of the amplifier 5'. Noises of short period are removed by filter 6.

The AC voltage filtered by filter 6 is transformed into a DC voltage by rectifier 7. The DC voltage corresponding to the peak value rectified by rectifier 7 is counter-proportionate to the absolute value $|Z|$ of the impedance of the deeper keratinous layer.

The DC voltage is digitized by an AD converter 9. The digitized signal is latched by a latch circuit 10 consecutively to be registered temporarily, and the digital output therefrom is outputted at a predetermined timing clocked by the timer 11 to computer 14 via an interface 13. The timing can be selected arbitrarily from the time when the electrode is abutted on the skin until the time when the measured value becomes stable. It is preferably 1–20 sec., and is, for instance, 5 seconds.

Computer 14 stores statistical data and compares the digital output which has been inputted with the statistical data.

Switch 15 is a means to switch the first circuit which uses the intermediate electrode 3'b as the common electrode and which is connected to the amplifier 5' and the second circuit which uses either one of the central electrode 3c and the outer electrode 3a as the common electrode and which is connected to the amplifier 5. By switching the switch 15, the moisture content on the surface keratinous layer can be detected. The structure and operation of the measurement is similar to the description made in relation to the prior art.

Figure 3:
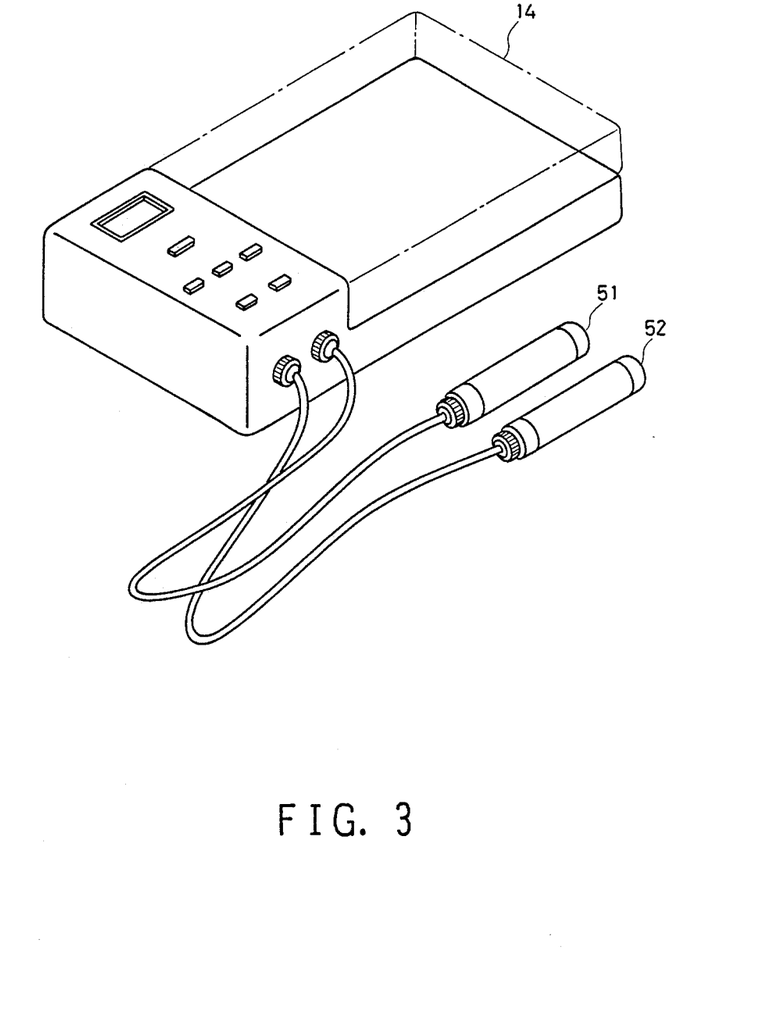

FIG. 3 is a perspective view of this invention measurement device. When the electrode 51 having the first circuit of the connection 3'c(R)-3'b(G)-3'a(S) and the central electrode 3'b as the common electrode is abutted on the skin, it can measure the moisture content of the deep keratinous layer while the measurement electrode 52 having the second circuit of the connection 3c(R)-3b(S)-3a(G) and either one of the central electrode 3c and the outer electrode 3a as the common electrode is abutted on the skin and measures the moisture content in the surface keratinous layer.

By manipulating the switch, the moisture content can be measured both in the deep layer and the surface layer of the keratinous layer to thereby enable more accurate diagnosis of the skin conditions.

Figure 4:
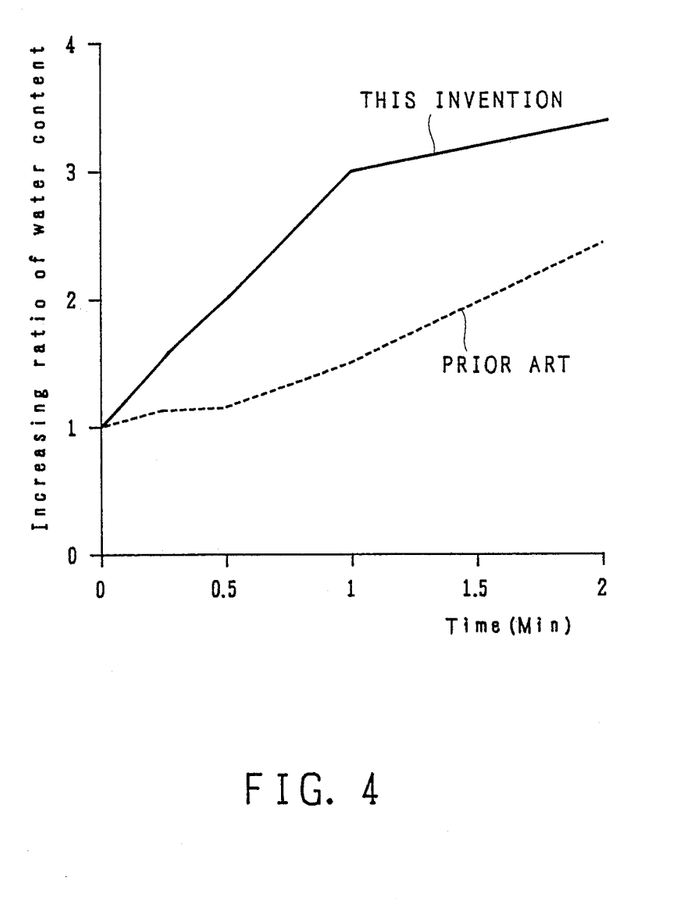

FIG. 4 is a graph to show moisture sensing characteristics. In simulation, five sheets of water permeable membrane (paraffin paper) were piled, and water was charged beneath the piled membranes. The characteristics were measured by closely attaching measurement electrodes 51 and 52 on the paper sheets.

The graph shows that as the water permeated, the measured value of the moisture content increased. The graph also reveals that the electrode 51 of this invention system could detect the same value in shorter time than the prior art electrode 52, indicating that moisture in the deeper layer was detected.

Figure 5:
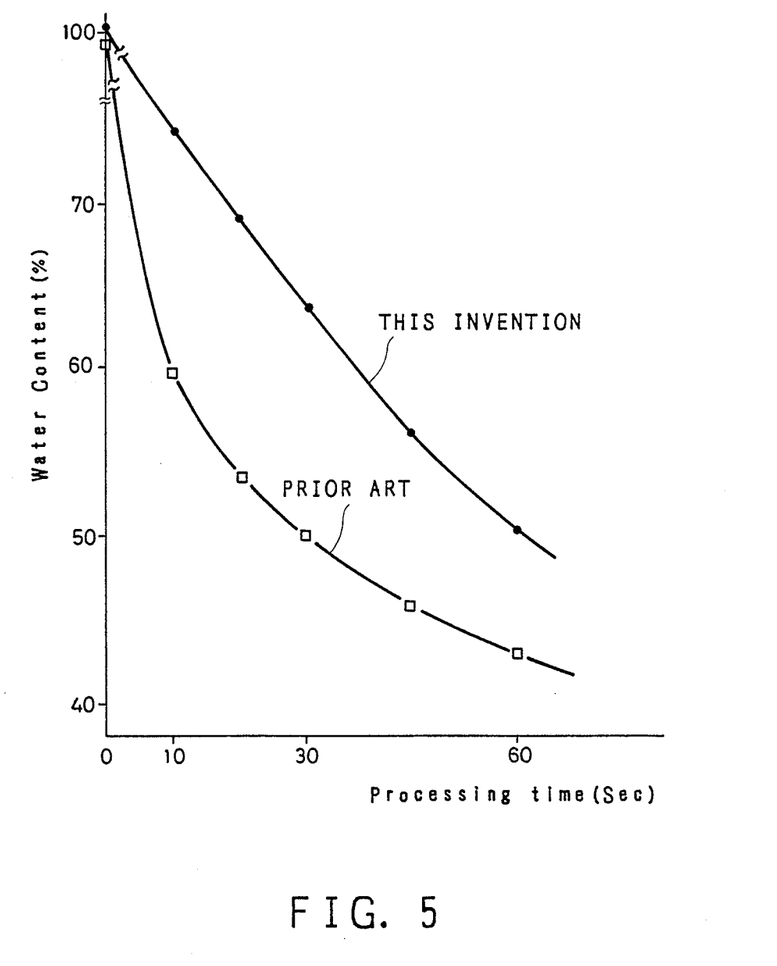

FIG. 5 is a graph to show the moisture detecting characteristics obtained from a test on the human skin. In the test dry gas ($N_2$ gas) was being blown onto the keratinous layer, and the moisture content was measured by the electrodes 51 and 52 which were attached closely on the skin.

The result of the test revealed that the effect of the dry gas was felt earlier in the case when the prior art electrode 52 was used than when this invention electrode 51 was used indicating that this invention system is less susceptible to the dry gas and can detect the moisture in the deeper keratinous layer of the skin.

Although the above embodiment connects the output from the buffer 2' to the outer electrode 3'a of the measurement electrode 3' and the input thereof is connected to the amplifier 5' of the central electrode 3'c, the central electrode 3'c and the outer electrode 3'a may be interchanged to have a similar effect. Although in the above embodiment, the filter 6 is connected to the output of the amplifier 5', it may be provided on the other side of the circuit 5' where low frequency current is supplied to the measurement electrode 3'. Electrodes 3 and 3' need not be circular but each electrode 3a, 3b, 3c, 3a', 3b' and 3c' is preferably a closed loop, e.g., oblong, triangular, square, irregular etc. shapes and electrodes 3 and 3' may be a mixture of such shapes.

What is claimed is:

1. A system for measuring moisture content in skin comprising:
    at least one measurement electrode structure of triple concentric electrodes including a central electrode, an intermediate electrode and an outer electrode, all of which can be abutted on the surface of said skin,
    generator means for supplying low frequency current between two of said electrodes,
    an amplifier connected to receive a voltage appearing between two of said electrodes, at least one of which is different than said two electrodes to which said generator means is connected,
    switch means for switching a connection between said amplifier and said electrodes and between said generator means and said electrodes such that different ones of said electrodes receive said low frequency current and different ones of said electrodes are connected to said amplifier, and
    means for displaying an output voltage of the amplifier.

2. A system as in claim 1 wherein the at least one measurement electrode structure includes two sets of closed loop electrodes including central, intermediate and outer electrodes, a first set of electrodes being connected to a first circuit and a second set being connected to a second circuit, said switch means switches between connection to said first and second circuits, and switches a connection of said amplifier between (a) said intermediate electrode and one of said central and outer electrodes, or (b) said central and outer electrodes.

3. A system as in claim 2 wherein said switch mans also switches said generator means such that said generator means supplies low frequency current between said intermediate electrode and one of said central and outer electrodes when said amplifier receives said voltage from between said central and outer electrodes.

4. A system for measuring moisture content in the skin comprising:

measurement electrode means comprising at least one set of three closed loop electrodes, each including a central electrode, an intermediate electrode and an outer electrode, all of which are adapted to be abutted to a surface of said skin, generator means for supplying low frequency current between a common electrode of each set and another one of said electrodes of each set, amplifier means for amplifying a voltage appearing between said common electrode of each set and a different electrode than said another one of said electrodes, circuit means for switching between a first circuit having said intermediate electrodes as said common electrode and a second circuit having said common electrode being one of said central and outer electrodes, and means for displaying the amplified voltage from said amplifier means.

5. A system as in claim 4 wherein the measurement electrode means includes two sets of closed loop electrodes including central, intermediate and outer electrodes, a first set of electrodes being connected to said first circuit and a second set being connected to said second circuit.

6. A system for measuring moisture content of skin comprising:

a first moisture detecting circuit including:

(a) a measurement electrode having a set of three closed loop electrodes including a central electrode, an intermediate electrode and an outer electrode, all of which are adapted to abut a surface of the skin;

(b) means for supplying a low frequency current between said intermediate electrode and one of said central and outer electrodes; and (c) means for receiving a voltage appearing between said intermediate electrode and the other of said central electrode and outer electrode and for amplifying said voltage;

a second measurement circuit including:

(a) a measurement electrode including a set of three closed loop electrodes including a central electrode, an intermediate electrode and an outer electrode, all of which are adapted to abut a surface of said skin;

(b) means for supplying a low frequency current between (1) one of said central electrode and said outer electrode, and (2) said intermediate electrode; and (c) amplifier means, receiving a voltage appearing between said central electrode and said outer electrode and for amplifying said voltage;

switching means for switching between said first measurement circuit and said second measurement circuit; and means, connected to an output of said switching means, for operating thereon.

* * * * *